(12) United States Patent
Lin et al.

(10) Patent No.: US 10,138,211 B2
(45) Date of Patent: Nov. 27, 2018

(54) CRYSTALLINE FORMS OF OLAPARIB AND MANUFACTURING PROCESSES THEREFOR

(71) Applicant: ScinoPharm Taiwan, Ltd., Shan-Hua, Tainan (TW)

(72) Inventors: Wen-Wei Lin, Tainan (TW); Tsung-Cheng Hu, Tainan (TW); Yuan-Chang Huang, Tainan (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 15/795,999

(22) Filed: Oct. 27, 2017

(65) Prior Publication Data
US 2018/0050991 A1   Feb. 22, 2018

Related U.S. Application Data

(62) Division of application No. 15/405,155, filed on Jan. 12, 2017, now abandoned.

(60) Provisional application No. 62/278,599, filed on Jan. 14, 2016.

(51) Int. Cl.
C07D 237/32 (2006.01)

(52) U.S. Cl.
CPC ........ C07D 237/32 (2013.01); *C07B 2200/13* (2013.01)

(58) Field of Classification Search
CPC .................................................. C07D 237/32
See application file for complete search history.

(56) References Cited

U.S. PATENT DOCUMENTS

| | | |
|---|---|---|
| 7,449,464 B2 | 11/2008 | Martin |
| 7,692,006 B2 | 4/2010 | Menear |
| 8,183,369 B2 | 5/2012 | Quigley |
| 8,247,416 B2 | 8/2012 | Menear |
| 8,475,842 B2 | 7/2013 | Bechtold |
| 2015/0284416 A1 | 10/2015 | Zhao |
| 2017/0174662 A1 | 6/2017 | Novo |
| 2017/0204067 A1 | 7/2017 | Lin |

FOREIGN PATENT DOCUMENTS

| | | |
|---|---|---|
| CN | 105439961 A | 3/2016 |
| JP | 2014-206389 A | 10/2014 |
| WO | WO-2008/047082 A2 | 4/2008 |
| WO | WO-2008/047082 A3 | 4/2008 |
| WO | WO-2009/050469 A1 | 4/2009 |
| WO | WO-2017/123156 A1 | 7/2017 |

OTHER PUBLICATIONS

International Search Report and Written Opinion dated Apr. 26, 2017, for PCT Application No. PCT/SG2017/050016, filed Jan. 13, 2017, 16 pages.
United States Patent and Trademark Office, Notice of Allowance for U.S. Appl. No. 15/405,155, dated Oct. 3, 2017, 6 pages.
Kakkar, et al., Isolation and Characterization of Ciprofloxacin-HCL Crystals, 1997, pp. 1063-1067.

*Primary Examiner* — Emily A Bernhardt
(74) *Attorney, Agent, or Firm* — Mintz, Levin, Cohn, Ferris, Glovsky and Popeo, P.C.

(57) ABSTRACT

In certain aspects, the invention provides crystalline forms of olaparib (4-[(3-[(4-cyclopropylcarbonyl)piperazin-4-yl]carbonyl)-4-fluorophenyl]methyl(2H)phthalazin-1-one). In related aspects, the invention provides processes for preparing the crystalline forms of olaparib. The processes include: forming a solution comprising crude olaparib and an organic solvent; adding an anti-solvent to the solution to form a slurry comprising a precipitate; isolating the precipitate; and drying the precipitate to obtain a crystalline form I of olaparib or a crystalline form II of olaparib.

18 Claims, 3 Drawing Sheets

CRYSTALLINE FORMS OF OLAPARIB AND MANUFACTURING PROCESSES THEREFOR

CROSS-REFERENCES TO RELATED APPLICATIONS

This application is a divisional application of U.S. patent application Ser. No. 15/405,155, filed Jan. 12, 2017, which claims the benefit of priority under 35 USC § 119(e) to U.S. Provisional Patent Application No. 62/278,599, filed Jan. 14, 2016, the contents of which are herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Olaparib is a phthalizinone compound developed as a poly(ADP-ribose) polymerase (PARP) inhibitor for use in treating cancers including ovarian, breast, and prostate cancers. Synthesis of olaparib and characterization of solids forms of the compound is disclosed in U.S. Pat. Nos. 8,247,416; 7,692,006; and 8,183,369. Specifically, U.S. Pat. No. 8,247,416 claims 4-[3-(4-cyclopropanecarbonyl-piperazine-1-carbonyl)-4-fluoro-benzyl]-2H-pthalazin-1-one (Compound A) substantially in crystalline form, and in particular in Form A. This patent also claims a method of synthesizing 4-[3-(4-cyclopropanecarbonyl-piperazine-1-carbonyl)-4-fluoro-benzyl]-2H-pthalazin-1-one from 2-fluoro-5-(4-oxo-3,4-dihydro-phthalazin-1-ylmethyl)-benzoic acid. U.S. Pat. No. 7,692,006 claims some methods of obtaining 4-[3-(4-cyclopropanecarbonyl-piperazine-1-carbonyl)-4-fluoro-benzyl]-2H-pthalazin-1-one (Compound A) as crystalline Form A. This patent also claims an intermediate of 2-fluoro-5-(4-oxo-3,4-dihydro-phthalazin-1-ylmethyl)-benzoic acid (ED) useful for preparing olaparib and a method of synthesizing the intermediate. As for U.S. Pat. No. 8,183,369, it is directed to 4-[3-(4-cyclopropanecarbonyl-piperazine-1-carbonyl)-4-fluoro-benzyl]-2H-pthalazin-1-one as crystalline From L and a method of obtaining it from 4-[3-(4-cyclopropanecarbonyl-piperazine-1-carbonyl)-4-fluoro-benzyl]-2H-pthalazin-1-one Form A. Olaparib has been approved by the U.S. Food and Drug Administration for treatment of women with advanced ovarian cancer associated with defective BRCA genes. New solid forms of olaparib are needed for enhancing the compound's demonstrated efficacy in the treatment of such cancers, as well as for improving processes for manufacture of pharmaceutical formulations that contain the drug. The present invention meets this need, providing novel crystalline forms of olaparib and processes for preparing the crystalline forms.

BRIEF SUMMARY OF THE INVENTION

In a first aspect, the invention provides crystalline form I of olaparib, which is characterized by the X-ray powder diffraction data, thermogravimetric analytical data, and differential scanning calorimetry data described herein.

In a second aspect, the invention provides a process for preparing the crystalline form I of olaparib. The process includes: forming a solution comprising crude olaparib and an organic solvent; adding an anti-solvent to the solution to form a slurry comprising a precipitate; isolating the precipitate; and drying the precipitate to obtain the crystalline form I of olaparib.

In a third aspect, the invention provides crystalline form II of olaparib, which is characterized by the X-ray powder diffraction data, thermogravimetric analytical data, and differential scanning calorimetry data described herein.

In a fourth aspect, the invention provides a process for preparing the crystalline form II of olaparib. The process includes: forming a solution comprising crude olaparib and an organic solvent; adding an anti-solvent to the solution to form a slurry comprising a precipitate; isolating the precipitate; and drying the precipitate to obtain the crystalline form II of olaparib.

DETAILED DESCRIPTION OF THE INVENTION

I. General

Figure 1:
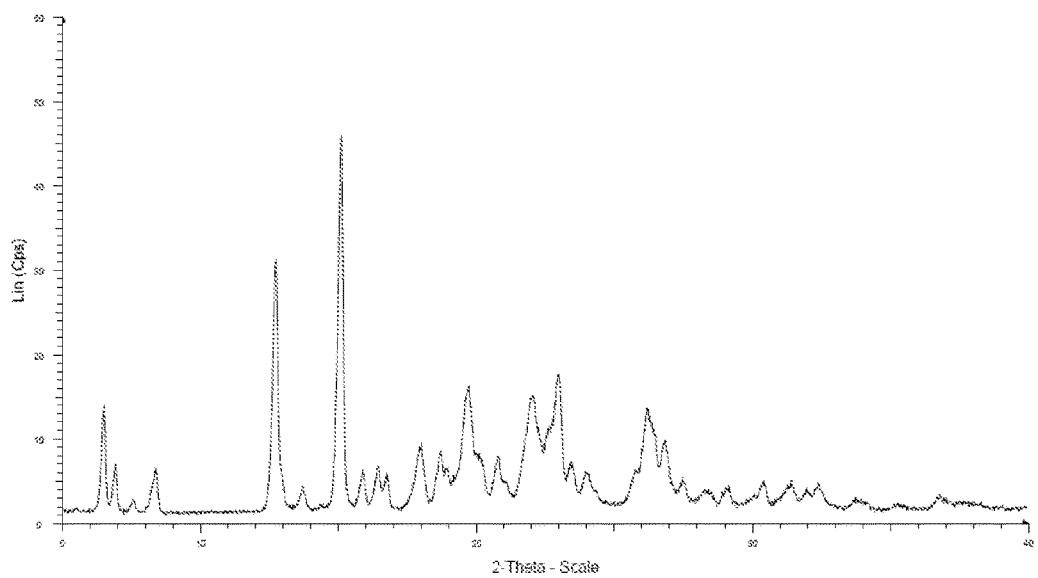
FIG. 1 shows the X-ray powder diffraction (XRPD) pattern recorded for the crystalline form I of olaparib.

The present invention provides novel solid forms of olaparib characterized by exceptional crystallinity and stability. Among other advantages, the novel solid forms can be prepared using high-yielding processes under mild conditions. In addition, the novel solid forms can be stored and/or used for manufacture of medicaments without converting to other forms such as non-crystalline forms.

II. Definitions

The term "olaparib" refers to 4-[(3-[(4-cyclopropylcarbonyl)piperazin-4-yl]carbonyl)-4-fluorophenyl]methyl(2H) phthalazin-1-one having the structure:

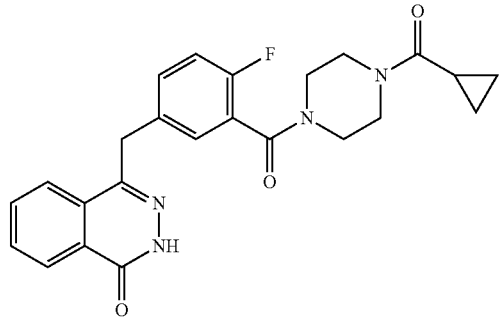

The term "crude" refers to a mixture containing a desired compound (e.g., olaparib) and at least one other species (e.g., a solvent, a reagent such as an acid or base, a starting material, or a byproduct of a reaction giving rise to the desired compound).

As used herein, the term "solvent" refers to a liquid substance capable of dissolving olaparib at a concentration of at least about 2.5% (w/w) at 60° C. The term "anti-solvent" refers to a liquid substance which is not capable of dissolving olaparib at a concentration of less than about 2.5% (w/w) at 60° C. More particularly, anti-solvents and solvents suitable for olaparib are shown in the table and summary below:

| Solubility of olaparib at 60° C. | Toluene | EtOH | ACN | Cyclohexane | IPA | THF | EA |
|---|---|---|---|---|---|---|---|
| | <16.9 mg/mL | 21-23 mg/mL | <16.2 mg/mL | <16.2 mg/mL | <16.2 mg/mL | <16.9 mg/mL | <16.2 mg/mL |
| | <1.9 wt % | 2.6-2.9 wt % | <2.1 wt % | <2.1 wt % | <2.1 wt % | <1.9 wt % | <1.8 wt % |
| | DMAc | Pyridine | Xylenes | n-heptane | water | n-butanol | MeOH |
| | >220.0 mg/mL | >210.0 mg/mL | <16.2 mg/mL | <16.2 mg/mL | <16.2 mg/mL | <16.9 mg/mL | 53-70 mg/mL |
| | >23.5 wt % | >21.5 wt % | <1.9 wt % | <2.4 wt % | <1.6 wt % | <2.1 wt % | 6.7-8.8 wt % |

| Solubility of olaparib at room temperature | AcOH | DMSO |
|---|---|---|
| | >210.0 mg/mL | >210.0 mg/mL |
| | >20.0 wt % | >19.1 wt % |

| Summary Solvents for olaparib | | Anti-solvents for olaparib |
|---|---|---|
| AcOH | EtOH | Toluene |
| DMSO | MeOH | ACN |
| DMAc | | Cyclohexane |
| Pyridine | | IPA |
| | | THF |
| | | EA |
| | | Xylenes |
| | | n-heptane |
| | | Water |
| | | n-butanol |

Suitable solvents described herein, refer to substances characterized with high solubility at 60° C.; while anti-solvents, generally considered 'poor solvents' refers to substances characterized with low solubility at 60° C. In the tables above, examples of good solvents include—but are not limited to—acetic acid, dimethylacetamide, dimethyl sulfoxide and pyridine. Examples of poor solvents (anti-solvents) include—but are not limited to—water, toluene, acetonitrile, cyclohexane, isopropanol, tetrahydrofuran, n-butanol, xylenes, ethyl acetate and n-heptane.

"Cooling" refers to the process of reducing the temperature of a substance or mixture of substances. "Heating" refers to the process of increasing the temperature of a substance or mixture of substances.

"Precipitating" refers to the process of causing a compound in a solution to coalesce into a solid form of the substance (i.e., a precipitate). The entirety of a compound in a solution, or any fraction thereof, can be caused to precipitate. The solid form of the substance can be amorphous or crystalline.

"Crystalline form" refers to a solid form of a compound wherein the constituent molecules are packed in a regularly ordered, repeating pattern. A crystalline form can include triclinic, monoclinic, orthorhombic, tetragonal, trigonal, hexagonal, and cubic crystal geometries. A crystalline form can contain one or more regions, i.e., grains, with distinct crystal boundaries. A crystalline solid can contain two or more crystal geometries.

"Amorphous form" refers to a solid form of a compound having no definite crystal structure, i.e., lacking a regularly ordered, repeating pattern of constituent molecules.

"Isolating" refers to the process of isolating at least a portion of a first substance (e.g., a precipitate) from a mixture containing the substance and at least one additional substance. In some instances, the isolated substance is substantially free at least one of the additional substances present in the original mixture.

"Drying" refers to the removal of a liquid, such as a solvent, from a substance. Drying is frequently conducted by heating the substance, reducing the pressure under which the substance is stored, or both.

The terms "about" and "around," as used herein to modify a numerical value, indicate a close range around that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

III. Crystalline Forms of Olaparib

In a first aspect, the invention provides a crystalline form I of olaparib. Crystalline form I of olaparib is characterized by an X-ray powder diffraction pattern including one or more peaks (i.e., 1, 2, 3, 4, 5, or 6 peaks) at 6.4, 12.7, 15.1, 19.7, 22.0, and 23.0 degrees 2θ (±0.2 degrees 2θ). In some embodiments, the X-ray powder diffraction pattern further comprises one or more peaks (i.e., 1, 2, 3, 4, 5, 6, or 7 peaks) at 6.9, 8.3, 15.9, 17.9, 20.8, 26.2, and 29.1 degrees 2θ (±0.2 degrees 2θ). In some embodiments, the X-ray powder diffraction pattern further comprises one or more peaks (i.e., 1, 2, 3, 4, 5, or 6 peaks) at 7.5, 13.7, 16.4, 18.7, 24.0, and 30.4 degrees 2θ (±0.2 degrees 2θ).

In some embodiments, crystalline form I of olaparib is characterized by an X-ray powder diffraction pattern including peaks at 6.4, 12.7, 15.1, 19.7, 22.0, and 23.0 degrees 2θ (±0.2 degrees 2θ). In some such embodiments, the X-ray powder diffraction pattern further comprises peaks at 6.9, 8.3, 15.9, 17.9, 20.8, 26.2, and 29.1 degrees 2θ (±0.2 degrees 2θ). In some such embodiments, the X-ray powder diffraction pattern further comprises peaks at 7.5, 13.7, 16.4, 18.7, 24.0, and 30.4 degrees 2θ (±0.2 degrees 2θ).

In some embodiments, crystalline form I of olaparib is characterized by an X-ray powder diffraction pattern including peaks at 6.4, 6.9, 7.5, 8.3, 12.7, 13.7, 15.1, 15.9, 16.4, 17.9, 18.7, 19.7, 20.8, 22.0, 23.0, 24.0, 26.2, 29.1, and 30.4 degrees 2θ (±0.2 degrees 2θ).

In some embodiments, crystalline form I of olaparib is characterized by an X-ray powder diffraction pattern comprising one or more peaks at 12.7, 15.1, 16.4, 23.0, 26.2, 26.8 and 27.5 degrees 2θ (±0.2 degrees 2θ).

In some embodiments, crystalline form I of olaparib is further characterized by a peak intensity at 23.0 degrees 2θ that is at least 15%, 20%, 25%, 30%, or 35% relative to the peak intensity at 15.1 degrees 2θ. In some embodiments, the peak intensity at 23.0 degrees 2θ is at least 30% relative to the peak intensity at 15.1 degrees 2θ.

In some embodiments, crystalline form I of olaparib is further characterized by a peak intensity at 23.0 degrees 2θ that is at least 10%, 15%, 20%, 25%, or 30% relative to the most intense peak, set at 100% intensity. In some embodiments, the peak intensity at 23.0 degrees 2θ is at least 30% relative to the most intense peak, set at 100% intensity.

In some embodiments, crystalline form I of olaparib is further characterized by a peak intensity at 26.2 degrees 2θ that is at least 10%, 15%, 20%, or 25% relative to the peak intensity at 15.1 degrees 2θ. In some embodiments, the peak intensity at 26.2 degrees 2θ is at least 20% relative to the peak intensity at 15.1 degrees 2θ.

In some embodiments, crystalline form I of olaparib is further characterized by a peak intensity at 26.2 degrees 2θ that is at least 10%, 15%, 20%, or 25% relative to the most intense peak, set at 100% intensity. In some embodiments, the peak intensity at 26.2 degrees 2θ is at least 20% relative to the most intense peak, set at 100% intensity.

In some embodiments, crystalline form I of olaparib is further characterized by a peak intensity at 26.8 degrees 2θ that is at least 10%, 15%, or 20% relative to the peak intensity at 15.1 degrees 2θ. In some embodiments, the peak intensity at 26.8 degrees 2θ is at least 15% relative to the peak intensity at 15.1 degrees 2θ.

In some embodiments, crystalline form I of olaparib is further characterized by a peak intensity at 26.8 degrees 2θ that is at least 10%, 15%, or 20% relative to the most intense peak, set at 100% intensity. In some embodiments, the peak intensity at 26.8 degrees 2θ is at least 15% relative to the most intense peak, set at 100% intensity.

In some embodiments, crystalline form I of olaparib is further characterized by a peak intensity at 16.4 degrees 2θ that is at least 10% relative to the peak intensity at 15.1 degrees 2θ.

In some embodiments, crystalline form I of olaparib is further characterized by a peak intensity at 16.4 degrees 2θ that is at least 10% relative to the most intense peak, set at 100% intensity.

In some embodiments, crystalline form I of olaparib is further characterized by a peak intensity at 27.5 degrees 2θ that is at least 10% relative to the peak intensity at 15.1 degrees 2θ.

In some embodiments, crystalline form I of olaparib is further characterized by a peak intensity at 27.5 degrees 2θ that is at least 10% relative to the most intense peak, set at 100% intensity.

In some embodiments, crystalline form I of olaparib is further characterized by one or more peaks at 8.3, 16.7, 19.7, and 22.0 degrees 2θ (±0.2 degrees 2θ). In some embodiments, crystalline form I of olaparib is further characterized by one or more peaks at 6.4, 6.9, 15.9, 17.9, 20.8, and 29.1 degrees 2θ (±0.2 degrees 2θ). In some embodiments, crystalline form I of olaparib is further characterized by one or more peaks at 7.5, 13.7, 16.4, 18.7, 24.0, and 30.4 degrees 2θ (±0.2 degrees 2θ).

In some embodiments, crystalline form I of olaparib is characterized by an X-ray powder diffraction substantially in accordance with FIG. 1.

Methods for collection of XRPD data are known in the art, and any such methods can be used for characterizing the crystalline forms of olaparib. For example, the X-ray powder diffraction patterns described herein can be generated using Cu Kα1 radiation.

In some embodiments, crystalline form I of olaparib is characterized by a weight loss ranging from about 3.5% to about 4.5% upon heating at around 150° C., as measured by thermal gravimetric analysis. In some such embodiments, the weight loss is measured using a sample weighing around 10-20 mg, which is subjected to temperatures ranging from 30° C. to 300° C. using a ramp of 10° C./min.

Figure 3:
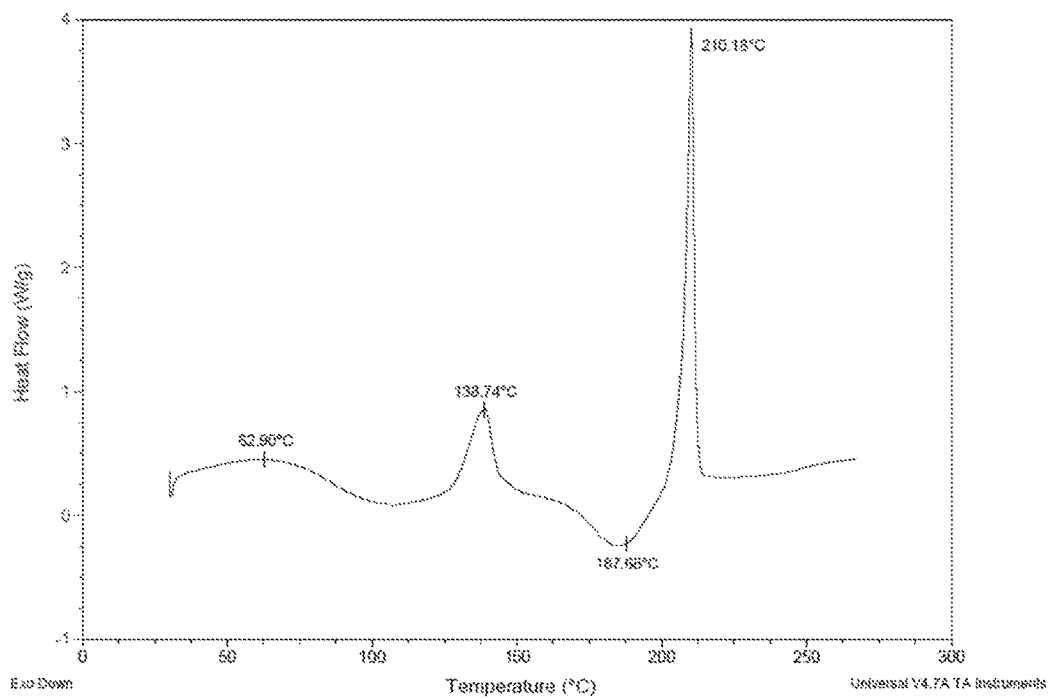
FIG. 3 shows the differential scanning calorimetry (DSC) thermogram recorded for crystalline form I of olaparib

In some embodiments, crystalline form I of olaparib is characterized by a differential scanning calorimetry thermogram comprising one or more endothermic peaks (i.e., 1, 2, or 3 endothermic peaks) at around 62.9, 138.7, and 210.2° C. In some such embodiments, the differential scanning calorimetry thermogram comprises endothermic peaks at around 62.9, 138.7, and 210.2° C. In some embodiments, crystalline form I of olaparib is characterized by a differential scanning calorimetry thermogram substantially in accordance with FIG. 3. In some such embodiments, a thermogram is recorded using a sample weighing around 1-10 mg, which is subjected to temperatures ranging from 30° C. to 270° C. using a ramp of 10° C./min.

In some embodiments, the crystalline form I of olaparib is a hydrated form. In some such embodiments, the hydrated form contains from about 3.5% (w/w) to about 4.5% (w/w) water.

In a second aspect, the invention provides a process for preparing crystalline form I of olaparib. The process includes:

a) forming a solution containing crude olaparib and an organic solvent;
b) adding an anti-solvent to the solution to form a slurry containing a precipitate;
c) isolating the precipitate; and
d) drying the precipitate to obtain the crystalline form I of olaparib.

In some embodiments, forming the solution comprises heating the solution. In some such embodiments, the method further includes cooling the slurry prior to isolating the precipitate.

In general, the crude olaparib used in the methods of the invention contains olaparib and at least one other substance associated with the synthesis and/or purification of the olaparib (e.g., a solvent; a starting material or intermediate; a reagent such as an acid or base; or a combination thereof). In general, the crude olaparib contains at least 50% (w/w) olaparib. The crude olaparib can include, for example, from about 50% (w/w) to about 55% (w/w) olaparib, or from about 55% (w/w) to about 60% (w/w) olaparib, or from about 60% (w/w) to about 65% (w/w) olaparib, or from about 65% (w/w) to about 70% (w/w) olaparib, or from about 70% (w/w) to about 75% (w/w) olaparib, or from about 75% (w/w) to about 80% (w/w) olaparib, or from about 80% (w/w) to about 85% (w/w) olaparib, or from about 85% (w/w) to about 90% (w/w) olaparib, or from about 90% (w/w) to about 95% (w/w) olaparib, or from about 95% (w/w) to about 99% (w/w) olaparib. The crude olaparib can contain from about 50% (w/w) to about 99% (w/w) olaparib, or from about 55% (w/w) to about 95% (w/w) olaparib, or from about 60% (w/w) to about 90% (w/w) olaparib, or from about 65% (w/w) to about 85% (w/w) olaparib, or from about 70% (w/w) to about 80% (w/w) olaparib. The crude olaparib can be obtained in a number of forms prior to dissolution according to the methods of the invention. For example, the crude compound can be a crystalline form, an amorphous form, a glass, or a foam.

Any solvent suitable for dissolving the crude olaparib can be used for forming the solution in the process of the invention. Examples of suitable solvents include, but are not limited to, methanol (MeOH); acetic acid (AcOH); N,N-dimethylacetamide (DMac); and dimethyl sulfoxide (DMSO). In some embodiments, the organic solvent is methanol.

Any amount of solvent suitable for dissolving the crude olaparib can be used for forming the solution. In general, the solvent will be used in amounts such that the solution contains the crude olaparib in an amount of at least around 5% (w/w). In some embodiments, the solution contains the crude olaparib in an amount ranging from about 5% (w/w) to about 30% (w/w). The solution can contain, for example, the crude olaparib in an amount ranging from about 5% (w/w) to about 10% (w/w), or from about 10% (w/w) to about 15% (w/w), or from about 15% (w/w) to about 20% (w/w), or from about 20% (w/w) to about 25% (w/w), or from about 25% (w/w) to about 30% (w/w). The solution can contain the crude olaparib in an amount ranging from about 5% (w/w) to about 29% (w/w), or from about 10% (w/w) to about 25% (w/w). The solution can contain the crude olaparib in an amount of about 5% (w/w), 10% (w/w), 15% (w/w), 20% (w/w), 25% (w/w), or 30% (w/w) olaparib.

In some embodiments, the solution contains methanol and the crude olaparib in an amount ranging from about 5% (w/w) to about 10% (w/w). In some embodiments, the solution contains acetic acid and the crude olaparib in an amount ranging from about 25% (w/w) to about 30% (w/w). In some embodiments, the solution contains N,N-dimethylacetamide and the crude olaparib in an amount ranging from about 10% (w/w) to about 15% (w/w). In some embodiments, the solution contains dimethyl sulfoxide and the crude olaparib in an amount ranging from about 15% (w/w) to about 20% (w/w).

As described above, forming the solution can include heating the solution. In some embodiments, the solution is heated to a temperature of at least about 50° C. The solution can be heated, for example, at a temperature ranging from about 50° C. to about 55° C., or from about 55° C. to about 60° C., or from about 60° C. to about 65° C., or from about 65° C. to about 70° C., or from about 70° C. to about 75° C., or from about 75° C. to about 80° C., or from about 80° C. to about 85° C., or from about 85° C. to about 90° C., or from about 90° C. to about 95° C., or from about 95° C. to about 100° C. The solution can be heated at a temperature ranging from about 50° C. to about 100° C., or from about 55° C. to about 95° C., or from about 60° C. to about 90° C., or from about 65° C. to about 85° C., or from about 70° C. to about 80° C. In some embodiments, forming the solution comprises heating the solution to a temperature ranging from about 55° C. to about 65° C.

One of skill in the art will appreciate that the heating temperature will depend, in part, on one or more factors including the particular organic solvent, the quantity of the solvent, and the level of purity of the crude olaparib. Such factors will also determine, to an extent, the length of time required to dissolve the crude compound. Any suitable length of the time can be used, ranging from a few minutes to several hours. For example, the mixture containing the crude olaparib and the organic solvent can be mixed, with or without heating, for about 10 minutes, or about 20 minutes, or 30 minutes, or about 40 minutes, or about 1 hour.

Any liquid substance suitable for precipitating olaparib can be used as the anti-solvent in the process for preparing olaparib as crystalline form I. In some embodiments, the anti-solvent is water. Any amount of the anti-solvent can be used for forming the slurry. In general, the anti-solvent will be used in an amount such that the slurry comprises at least about 50% (w/w) anti-solvent. For example, the slurry can contain the anti-solvent in an amount ranging from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w), or from about 80% (w/w) to about 85% (w/w), or from about 85% (w/w) to about 90% (w/w), or from about 90% (w/w) to about 95% (w/w), or from about 95% (w/w) to about 99% (w/w). The slurry can contain the anti-solvent in an amount ranging from about 50% (w/w) to about 99% (w/w), or from about 55% (w/w) to about 95% (w/w), or from about 60% (w/w) to about 90% (w/w), or from about 65% (w/w) to about 85% (w/w), or from about 70% (w/w) to about 80% (w/w).

In some embodiments, the slurry comprises the anti-solvent in an amount ranging from about 60% (w/w) to about 95% (w/w). In some embodiments, the slurry contains methanol; olaparib in an amount ranging from about 5% (w/w) to about 10% (w/w); and water in an amount ranging from about 70% (w/w) to about 75% (w/w). In some embodiments, the slurry contains acetic acid; olaparib in an amount ranging from about 25% (w/w) to about 30% (w/w); and water in an amount ranging from about 90% (w/w) to about 95% (w/w). In some embodiments, the slurry contains N,N-dimethylacetamide; the crude olaparib in an amount ranging from about 10% (w/w) to about 15% (w/w); and water in an amount ranging from about 85% (w/w) to about 90% (w/w). In some embodiments, the slurry contains dimethyl sulfoxide; the crude olaparib in an amount ranging from about 15% (w/w) to about 20% (w/w); and water in an amount ranging from about 85% (w/w) to about 90% (w/w).

As described above, the method can include heating the crude olaparib solution and cooling the olaparib slurry prior to isolating the olaparib precipitate. Typically, the slurry will be cooled to a temperature below 30° C. The slurry can be cooled, for example, to a temperature around 25° C., around 20° C., or around 4° C. One of skill in the art will appreciate that the cooling temperature can depend, in part, on the solubility of the olaparib in the solvent/anti-solvent mixture, as well as the quantities of the solvent and anti-solvent used in the process. The cooling can be conducted over any suitable length of time, typically ranging from a few minutes to several hours.

Isolating the precipitated olaparib from the solvent/anti-solvent mixture can be accomplished after slurry formation by a number of techniques, including passing the mixture through a filter to isolate the solid material or centrifuging the mixture and removing the solvent/anti-solvent supernatant. Alternatively, the slurry can be frozen and the solvent/anti-solvent mixture can be removed from the precipitate via sublimation. In some embodiments, the process further includes washing the isolated precipitate. Washing can be conducted by triturating the precipitate with additional portions of the anti-solvent or a solvent/anti-solvent mixture. The washing can remove residual impurities, if present. In some embodiments, the process for preparing olaparib as crystalline form I includes washing the isolated precipitate with one or more portions of water or one or more portions of a water/methanol solution.

After isolating the precipitated olaparib, with or without additional washing steps, the olaparib is dried to remove solvent and anti-solvent from the solid material. Drying can be conducted under ambient temperature and pressure. Evaporation of solvent and anti-solvent can be promoted by contacting the solid material with a stream of air, nitrogen, argon, or other another gas or gas mixture. In some embodiments, the precipitate is dried under reduced pressure. In some embodiments, the precipitate is dried under reduced pressure and elevated temperatures. In some embodiments, drying the precipitate comprises heating the precipitate to a temperature ranging from about 30° C. to about 80° C. In some embodiments, drying the precipitate comprises heating the precipitate to a temperature ranging from about 40° C. to about 70° C. Any suitable pressure, temperature, and drying time can be used to partially or fully remove the solvent and the anti-solvent from the precipitated olaparib. Drying can be conducted, for example, under reduced pressure and elevated temperature until the weight of the olaparib remains constant.

In a third aspect, the invention provides a crystalline form II of olaparib. In some embodiments, crystalline form II of olaparib is characterized by an X-ray powder diffraction pattern including one or more peaks (i.e., 1, 2, 3, 4, 5, or 6 peaks) at 6.8, 11.3, 14.4, 20.9, 21.7, and 25.0 degrees 2θ (±0.2 degrees 2θ). In some embodiments, the X-ray powder diffraction pattern further includes one or more peaks (i.e., 1, 2, 3, 4, 5, or 6 peaks) at 10.4, 12.3, 14.5, 20.4, 23.4, and 26.4 degrees 2θ (±0.2 degrees 2θ). In some embodiments, the X-ray powder diffraction pattern further includes one or more peaks (i.e., 1, 2, 3, 4, 5, 6, or 7 peaks) at 16.0, 17.4, 18.5, 24.0, 25.0, 28.2, and 34.3 degrees 2θ (±0.2 degrees 2θ).

In some embodiments, crystalline form II of olaparib is characterized by an X-ray powder diffraction pattern including peaks at 6.8, 11.3, 14.4, 20.9, 21.7, and 25.0 degrees 2θ (±0.2 degrees 2θ). In some such embodiments, the X-ray powder diffraction pattern further includes peaks at 10.4, 12.3, 14.5, 20.4, 23.4, and 26.4 degrees 2θ (±0.2 degrees 2θ). In some such embodiments, the X-ray powder diffraction pattern further includes peaks at 16.0, 17.4, 18.5, 24.0, 25.0, 28.2, and 34.3 degrees 2θ (±0.2 degrees 2θ).

Figure 4:
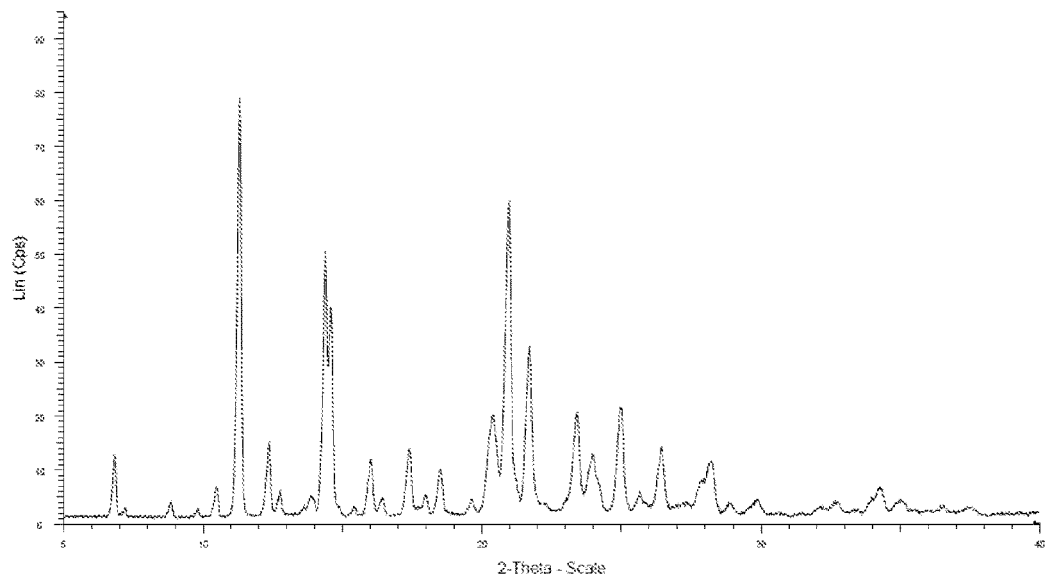
FIG. 4 shows the XRPD pattern recorded for the crystalline form II of olaparib.
Figure 5:
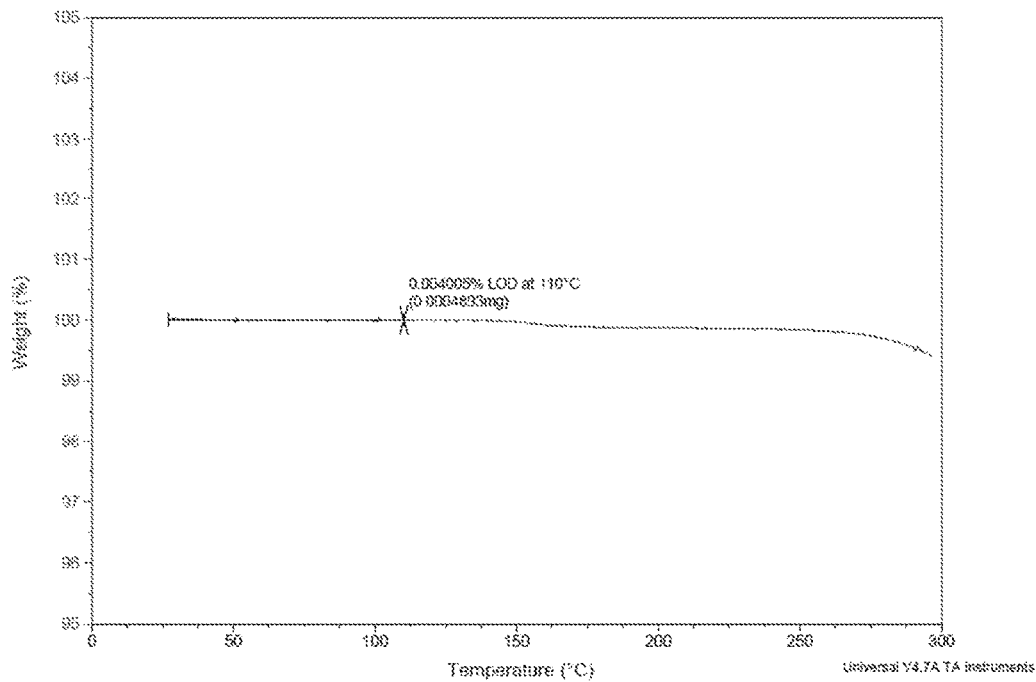
FIG. 5 shows the TGA thermogram recorded for crystalline form II of olaparib.

In some embodiments, crystalline form II of olaparib is characterized by an X-ray powder diffraction pattern including peaks at 6.8, 10.4, 12.3, 11.3, 14.4, 14.5, 16.0, 17.4, 18.5, 20.4, 20.9, 21.7, 23.4, 24.0, 25.0, 26.4, 28.2, and 34.3 degrees 2θ (±0.2 degrees 2θ). In some embodiments, form II of olaparib is characterized by an X-ray powder diffraction pattern substantially in accordance with FIG. 4.

In some embodiments, form II of olaparib is further characterized by essentially no weight loss upon heating to around 200° C., as measured by thermal gravimetric analysis (TGA).

Figure 6:
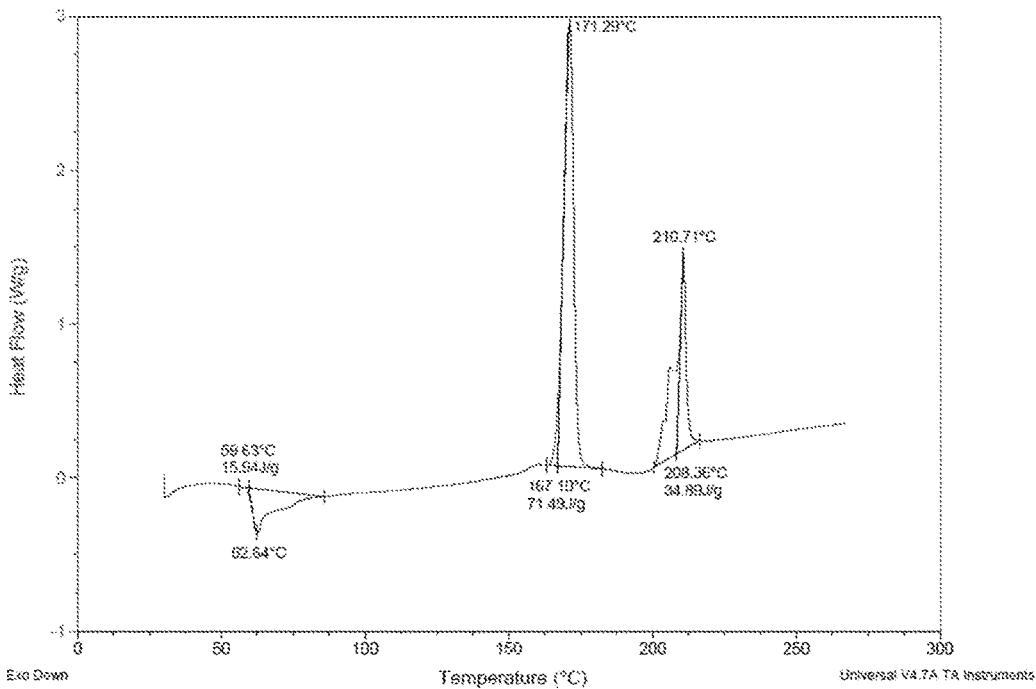
FIG. 6 shows the DSC thermogram recorded for crystalline form II of olaparib.

In some embodiments, form II of olaparib is further characterized by a differential scanning calorimetry thermogram comprising one or two endothermic peaks at about 171.3° C. and 210.7° C. In some such embodiments, the differential scanning calorimetry thermogram comprises two endothermic peaks at about 171.3° C. and 210.7° C. In some embodiments, form II of olaparib is further characterized by a differential scanning calorimetry thermogram substantially in accordance with FIG. 6.

In some embodiments, the crystalline form II of olaparib is an anhydrous form.

In a fourth aspect, the invention provides a process for preparing the crystalline form II of olaparib. The process includes:
i) forming a solution comprising crude olaparib and an organic solvent;
ii) adding an anti-solvent to the solution to form a slurry comprising a precipitate;
iii) isolating the precipitate; and
iv) drying the precipitate to obtain the crystalline form II of olaparib.

The crude olaparib solution can be prepared as described above. In some embodiments, the solution contains methanol and the crude olaparib in an amount ranging from about 5% (w/w) to about 10% (w/w). Examples of anti-solvents include—but are not limited to—n-hexane, n-heptane, petroleum ether, n-octane, cyclohexane, benzene, toluene, 1,4-dioxane, chloroform, and diethyl ether, can be useful in the methods of the invention. In some embodiments, the anti-solvent is selected from n-heptane, n-hexane, cyclohexane, petroleum ether, and combinations thereof. In some embodiments, the anti-solvent is n-heptane.

Any amount of the anti-solvent suitable for precipitating olaparib can be used for forming the slurry. In general, the anti-solvent will be used in an amount such that the slurry comprises at least about 50% (w/w) anti-solvent. For example, the slurry can contain the anti-solvent in an amount ranging from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w), or from about 80% (w/w) to about 85% (w/w), or from about 85% (w/w) to about 90% (w/w), or from about 90% (w/w) to about 95% (w/w), or from about 95% (w/w) to about 99% (w/w). The slurry can contain the anti-solvent in an amount ranging from about 50% (w/w) to about 99% (w/w), or from about 55% (w/w) to about 95% (w/w), or from about 60% (w/w) to about 90% (w/w), or from about 65% (w/w) to about 85% (w/w), or from about 70% (w/w) to about 80% (w/w).

In some embodiments, the slurry comprises the anti-solvent in an amount ranging from about 60% (w/w) to about 95% (w/w). In some embodiments, the slurry contains methanol; olaparib in an amount ranging from about 5% (w/w) to about 10% (w/w); and n-heptane in an amount ranging from about 60% (w/w) to about 65% (w/w).

Heating and cooling can be employed in the dissolution and precipitation steps as described above. The slurry containing the precipitated olaparib and the anti-solvent can be cooled, for example, to a temperature around 25° C., around 20° C., or around 4° C. In some embodiments, the slurry containing the precipitated olaparib and the anti-solvent is cooled to a temperature of around 10° C. or less. The process for preparing olaparib as crystalline form II generally includes isolation, optional washing, and drying of the precipitated olaparib as described above.

IV. Examples

The following examples describe crystalline forms of olaparib and processes suitable for their preparation on a laboratory-scale or an industrial scale. The present invention includes, but is not limited to, the embodiments described in the examples.

Example 1. Methods for Characterizing Solid Forms of Olaparib

X-Ray Powder Diffraction.

Powder X-ray Diffraction patterns were collected on a Bruker AXS D8 Advance diffractometer using Cu Kα1 radiation (40 kV, 40 mA), a 0-20 goniometer, a Ge monochromator, and a LynxEye detector. XRPD patterns were collected under ambient condition. The scanning parameters included an angular range of 5-40°, a step size of 0.02°, and a scan speed of 0.6 sec/step.

Thermal Gravimetric Analysis (TGA).

TGA data was collected on a TA Instrument Q500 TGA. Each sample (15-20 mg) was loaded onto a pre-tared platinum crucible and the balance and furnace were purged with nitrogen prior to the analysis with a flow rate set as 40±5 and 60±5 mL/min, respectively. The heating process was programmed to start from 30° C. and stop at 300° C. with a 10° C./min ramp.

Differential Scanning Calorimetry (DSC).

DSC data was collected on a TA Instrument MDSC Q200. Each sample (2-5 mg) was loaded onto a hermetic pan and the analysis was carried out under a constant flow of nitrogen (60 mL/min). The heating process was programmed to start from 30° C. and stop at 270° C. with a 10° C./min ramp.

Example 2: The Preparation of the Crystalline Form I of Olaparib 4 g of olaparib was dissolved in 84 mL of methanol at about 60° C. The resulting mixture was stirred until complete dissolution was observed. About 168 mL of water was added to the solution at about 60° C. The resulting suspension was cooled to room temperature (about 25° C.) and filtered to obtain a wet cake. The wet cake was dried by nitrogen purging for about 1 hour, followed by drying at 70° C. in an oven under vacuum for 21 hours to provide the crystalline form I of olaparib. The XRPD pattern of the dried olaparib form I was recorded. See, FIG. 1. The XRPD data is summarized in below in Table 1.

TABLE 1

PXRD peak data for olaparib crystalline Form I

| Angle (2θ) | Intensity (Cps) | Intensity (%) |
| --- | --- | --- |
| 6.4 | 14 | 30.4 |
| 6.9 | 6.86 | 15 |
| 7.5 | 2.77 | 6 |
| 8.3 | 6.4 | 13.9 |
| 12.7 | 31.2 | 68 |
| 13.7 | 4.26 | 9.3 |
| 15.1 | 45.9 | 100 |
| 15.9 | 6.23 | 13.6 |
| 16.4 | 6.67 | 14.5 |
| 16.7 | 5.94 | 12.9 |
| 17.9 | 8.92 | 19.5 |
| 18.7 | 8.46 | 18.4 |
| 19.7 | 15.8 | 34.5 |
| 20.8 | 7.78 | 17 |
| 22 | 15.1 | 32.8 |
| 23 | 17.6 | 38.3 |
| 23.4 | 7.25 | 15.8 |
| 24 | 5.89 | 12.8 |
| 26.2 | 13.4 | 29.2 |
| 26.8 | 9.51 | 20.7 |
| 27.5 | 5.28 | 11.5 |
| 28.3 | 3.76 | 8.2 |
| 29.1 | 3.91 | 8.5 |
| 30.4 | 4.98 | 10.9 |
| 31.4 | 4.51 | 9.8 |
| 32 | 4.09 | 8.9 |
| 32.4 | 4.7 | 10.2 |

Example 3: The Preparation of the Crystalline Form I of Olaparib 0.2 g of olaparib was dissolved in 4.5 mL of methanol at about 60° C. The resulting mixture was stirred until complete dissolution was observed, and the mixture was added to about 10 mL of water at room temperature (about 25° C.). The resulting suspension was filtered to obtain a wet cake. The wet cake was dried by nitrogen purging for about 1 hour, followed by drying at 70° C. an oven under vacuum for 23 hours to provide the crystalline form I of olaparib. The XRPD pattern of the dried olaparib was recorded, which was substantially identical to the pattern illustrated in FIG. 1.

Example 4: The Preparation of the Crystalline Form I of Olaparib 4 g of olaparib was dissolved in 10 mL of acetic acid at room temperature (about 25° C.). The resulting mixture was stirred until complete dissolution was observed, and about 188 mL of water was added at room temperature. The resulting suspension was filtered to obtain a wet cake. The wet cake was dried by nitrogen purging for about 1 hour, followed by drying at 70-80° C. in an oven under vacuum for 5 days to provide the crystalline form I of olaparib. The XRPD pattern of the dried olaparib was recorded, which was substantially identical to the pattern illustrated in FIG. 1.

Example 5: The Preparation of the Crystalline Form I of Olaparib 0.2 g of olaparib was dissolved in 1.5 mL of DMAc at room temperature (about 25° C.). The resulting mixture was stirred till complete dissolution was observed, and about 10 mL of water was added at room temperature. The resulting suspension was filtered to obtain a wet cake. The wet cake was dried by nitrogen purging for about 1 hour, followed by drying at 70° C.-80° C. in an oven under vacuum for 17.5 hours to provide the crystalline form I of olaparib. The XRPD pattern of the dried olaparib was recorded, which was substantially identical to the pattern illustrated in FIG. 1.

Example 6: The Preparation of the Crystalline Form I of Olaparib 0.2 g of olaparib was dissolved in 1 mL of DMSO at room temperature (about 25° C.). The resulting mixture was stirred till complete dissolution was observed, and about 10 mL of water was added at room temperature. The resulting suspension was filtered to obtain a wet cake. The wet cake was dried by nitrogen purging for about 1 hour, followed by drying at 70° C.-80° C. in an oven under vacuum for 17.5 hours to provide the crystalline form I of olaparib. The XRPD pattern of the dried olaparib was recorded, which was substantially identical to the pattern illustrated in FIG. 1.

Figure 2:
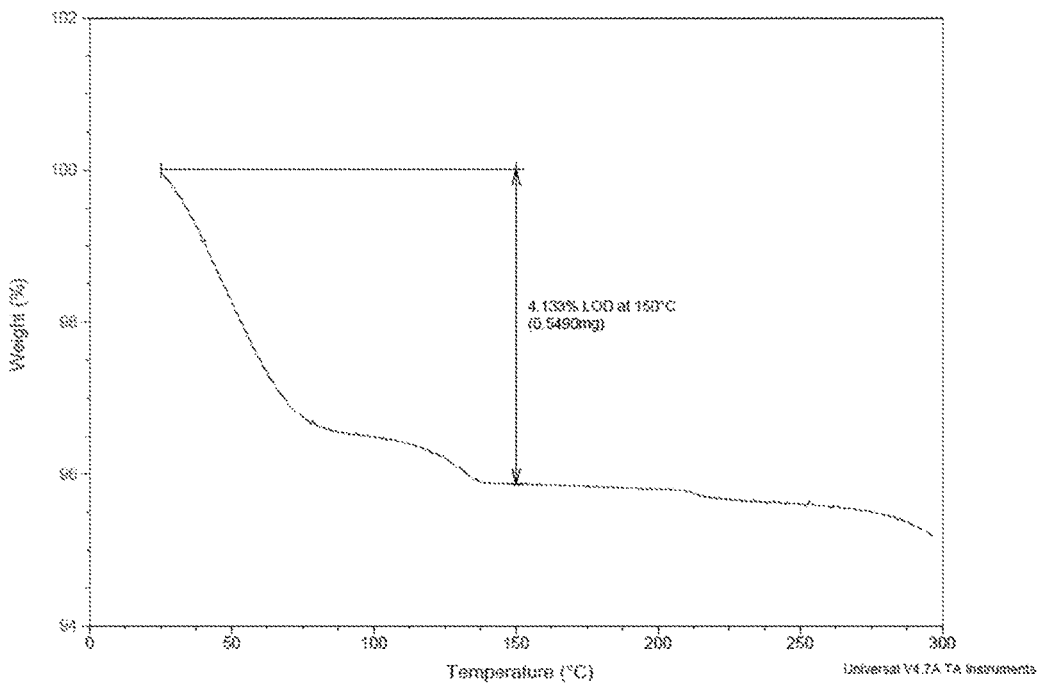
FIG. 2 shows the thermogravimetric analysis (TGA) thermogram recorded for crystalline form I of olaparib

Example 7: The Preparation of the Crystalline Form II of Olaparib 0.2 g of olaparib was dissolved in 4.5 mL of methanol at about 60° C. The resulting mixture was stirred till complete dissolution was observed, and about 9 mL of n-heptane was added at about 60° C. The resulting suspension was cooled to room temperature (about 25° C.) and filtered to obtain a wet cake. The wet cake was dried by nitrogen purging for about 1 hour, followed by drying at 70° C. in an oven under vacuum for 19 hours to provide the crystalline form II of olaparib. The XRPD pattern of the dried olaparib was recorded. See, FIG. 2.

TABLE 2

PXRD peak data for olaparib crystalline Form II

| Angle (2θ) | Intensity (Cps) | Intensity (%) |
| --- | --- | --- |
| 6.8 | 12.7 | 16 |
| 7.1 | 2.84 | 3.6 |
| 8.8 | 4.12 | 5.2 |
| 9.8 | 2.73 | 3.5 |
| 10.4 | 6.69 | 8.5 |
| 11.3 | 79 | 100 |
| 12.3 | 15 | 19 |
| 12.7 | 6.09 | 7.7 |
| 13.9 | 4.97 | 6.3 |
| 14.4 | 50.6 | 64.1 |
| 14.5 | 40 | 50.7 |
| 15.4 | 2.96 | 3.7 |
| 16 | 11.7 | 14.9 |
| 16.4 | 4.65 | 5.9 |
| 17.4 | 13.9 | 17.6 |
| 18 | 5.15 | 6.5 |
| 18.5 | 9.92 | 12.6 |
| 19.6 | 4.4 | 5.6 |
| 20.4 | 20.1 | 25.4 |
| 20.9 | 59.9 | 75.9 |
| 21.7 | 32.8 | 41.6 |
| 23.4 | 20.3 | 25.8 |
| 24 | 12.8 | 16.2 |
| 25 | 21.5 | 27.2 |
| 25.7 | 5.77 | 7.3 |
| 26.4 | 14.1 | 17.8 |
| 28.2 | 11.4 | 14.5 |
| 28.9 | 3.67 | 4.6 |
| 29.9 | 4.27 | 5.4 |
| 34.3 | 6.56 | 8.3 |

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. Crystalline form II of olaparib, characterized by an X-ray powder diffraction pattern comprising peaks at 6.8, 11.3, 14.4, 20.9, 21.7, and 25.0 degrees 2θ (±0.2 degrees 2θ); wherein the crystalline form II of olaparib is an anhydrous form.

2. The crystalline form II of olaparib according to claim 1, wherein the X-ray powder diffraction pattern further comprises peaks at 10.4, 12.3, 14.5, 20.4, 23.4, and 26.4 degrees 2θ (±0.2 degrees 2θ).

3. The crystalline form II of olaparib according to claim 1, wherein the X-ray powder diffraction pattern further comprises peaks at 16.0, 17.4, 18.5, 24.0, 25.7, 28.2, and 34.3 degrees 2θ (±0.2 degrees 2θ).

4. Crystalline form II of olaparib according to claim 1, characterized by a powder X-ray diffraction pattern substantially in accordance with FIG. 4.

5. The crystalline form II of olaparib according to claim 1, further characterized by essentially no weight loss upon heating to around 200° C., as measured by thermal gravimetric analysis.

6. The crystalline form II of olaparib according to claim 1, further characterized by a differential scanning calorimetry thermogram comprising endothermic peaks at about 171.3° C. and 210.7° C.

7. The crystalline form II of olaparib according to claim 6, wherein the differential scanning calorimetry thermogram is substantially in accordance with FIG. 6.

8. The crystalline form II of olaparib according to claim 4, further characterized by a differential scanning calorimetry thermogram substantially in accordance with FIG. 6.

9. A process for preparing the crystalline form II of olaparib of claim 1, the process comprising:
 i) forming a solution comprising crude olaparib and an organic solvent;
 ii) adding an anti-solvent to the solution to form a slurry comprising a precipitate;
 iii) isolating the precipitate; and
 iv) drying the precipitate to obtain the crystalline form II of olaparib;
wherein the organic solvent is methanol and the anti-solvent is selected from the group consisting of n-heptane, n-hexane, cyclohexane, petroleum ether, and combinations thereof.

10. The process of claim 9, wherein forming the solution comprises heating the solution.

11. The process of claim 10, wherein the solution is heated to a temperature ranging from about 55° C. to about 65° C.

12. The process of claim 10, further comprising cooling the slurry prior to isolating the precipitate.

13. The process of claim 12, wherein the slurry is cooled to a temperature of around 10° C. or less.

14. The process of claim 10, wherein the anti-solvent is n-hexane.

15. The process of claim 10, wherein the solution comprises the crude olaparib in an amount ranging from about 5% (w/w) to about 30% (w/w).

16. The process of claim 10, wherein the slurry comprises the anti-solvent in an amount ranging from about 60% (w/w) to about 95% (w/w).

17. The process of claim 10, wherein drying the precipitate comprises heating precipitate to a temperature ranging from about 30° C. to about 80° C.

18. The process of claim 10, further comprising washing the precipitate prior to drying the precipitate.

* * * * *